United States Patent
Zhan et al.

(10) Patent No.: US 10,952,698 B2
(45) Date of Patent: Mar. 23, 2021

(54) METHOD AND APPARATUS WITH PHOTON-COUNTING X-RAY DETECTORS HAVING FOR SPATIALLY-VARYING ENERGY BIN THRESHOLDS

(71) Applicant: CANON MEDICAL SYSTEMS CORPORATION, Otawara (JP)

(72) Inventors: Xiaohui Zhan, Vernon Hills, IL (US); Kevin Christopher Zimmerman, Vernon Hills, IL (US); Cai Liang, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 16/388,695

(22) Filed: Apr. 18, 2019

(65) Prior Publication Data
US 2020/0330065 A1    Oct. 22, 2020

(51) Int. Cl.
*A61B 6/00* (2006.01)
*G01T 1/36* (2006.01)
*A61B 6/03* (2006.01)

(52) U.S. Cl.
CPC .......... *A61B 6/585* (2013.01); *A61B 6/032* (2013.01); *A61B 6/4035* (2013.01); *A61B 6/4241* (2013.01); *G01T 1/36* (2013.01)

(58) Field of Classification Search
CPC ....... A61B 6/585; A61B 6/032; A61B 6/4241; A61B 6/4035; G01T 1/36
See application file for complete search history.

(56) References Cited

U.S. PATENT DOCUMENTS

| | | | |
|---|---|---|---|
| 2002/0070365 A1* | 6/2002 | Karellas | A61B 6/505 250/581 |
| 2002/0097831 A1* | 7/2002 | Cheng | A61B 6/0421 378/20 |
| 2005/0259784 A1* | 11/2005 | Wu | A61B 6/032 378/19 |
| 2006/0109953 A1 | 5/2006 | Walter et al. | |
| 2014/0334600 A1* | 11/2014 | Lee | A61B 6/4241 378/62 |

(Continued)

OTHER PUBLICATIONS

Ralf Gutjahr, et al. "Human imaging with photon-counting-based CT at clinical dose levels: Contrast-to-noise ratio and cadaver studies", HHS Public Access, Published in final edited form as: Invest Radiol. Jul. 2016; 51(7): 421-429. doi:10.1097/RLI.0000000000000251.

*Primary Examiner* — Chih-Cheng Kao
(74) *Attorney, Agent, or Firm* — Oblon, McClelland, Maier & Neustadt, L.L.P.

(57) ABSTRACT

A method and apparatuses are provided to estimate, for two or more detector elements in an array of photon-counting detector elements, respective energy spectra of an X-ray beam incident on the corresponding detector elements from an X-ray source, the energy spectra being estimated by modeling X-ray attenuation as a function of X-ray energy when an X-ray beam is transmitted through a filter and set, for each detector element of the two or more detector elements, a first energy threshold of an energy range that is detected by the each detector element, the first energy threshold of the each detector element being based on the estimated energy spectra of the each detector element.

18 Claims, 7 Drawing Sheets

(56) References Cited

U.S. PATENT DOCUMENTS

| | | | |
|---|---|---|---|
| 2015/0287221 A1* | 10/2015 | Takayama | A61B 6/032 378/91 |
| 2015/0313569 A1* | 11/2015 | Stevens | A61B 6/542 378/8 |
| 2016/0095561 A1 | 4/2016 | Tamura | |
| 2016/0202364 A1 | 7/2016 | Wang et al. | |

* cited by examiner

METHOD AND APPARATUS WITH PHOTON-COUNTING X-RAY DETECTORS HAVING FOR SPATIALLY-VARYING ENERGY BIN THRESHOLDS

BACKGROUND

Field

Embodiments described herein relate generally to configurable energy threshold settings for detector pixels in photon-counting X-ray detectors, and, more particularly, to computed tomography (CT) systems and methods to optimally adjust a plurality of energy threshold values for respective detectors in the detector array in accordance with the energy spectra at corresponding points in the X-ray beam.

Description of the Related Art

Computed tomography (CT) systems and methods are widely used, particularly for medical imaging and diagnosis. CT systems generally create projection images of one or more sectional slices through a subject's body. A radiation source, such as an X-ray source, irradiates the body from one side. A collimator, generally adjacent to the X-ray source, limits the angular extent of the X-ray beam, so that radiation impinging on the body is substantially confined to a planar region (i.e., an X-ray projection plane) defining a cross-sectional slice of the body. At least one detector (and generally many more than one detector) on the opposite side of the body receives radiation transmitted through the body in the projection plane. The attenuation of the radiation that has passed through the body is measured by processing electrical signals received from the detector. In some implementations a multi slice detector configuration is used, providing a volumetric projection of the body rather than planar projections.

Typically the X-ray source is mounted on a gantry that revolves about a long axis of the body. The detectors are likewise mounted on the gantry, opposite the X-ray source. A cross-sectional image of the body is obtained by taking projective attenuation measurements at a series of gantry rotation angles, transmitting the projection data/sinogram to a processor via the slip ring that is arranged between a gantry rotor and stator, and then processing the projection data using a CT reconstruction algorithm (e.g., inverse Radon transform, a filtered back-projection, Feldkamp-based cone-beam reconstruction, iterative reconstruction, or other method). For example, the reconstructed image can be a digital CT image that is a square matrix of elements (pixels), each of which represents a volume element (a, volume pixel or voxel) of the patient's body. In some CT systems, the combination of translation of the body and the rotation of the gantry relative to the body is such that the X-ray source traverses a spiral or helical trajectory with respect to the body. The multiple views are then used to reconstruct a CT image showing the internal structure of the slice or of multiple such slices.

Energy-integrating detectors (Ms) have been used to measure CT projection data. Alternatively, photon-counting detectors (PCDs) provide many advantages compared to energy-integrating detectors, including their capacity for performing spectral CT and the ability to divide the scan area into many smaller "pixels" of detectors for greater resolution. While semiconductor-based PCDs provide unique advantages for spectral CT, they also create unique challenges. For example, PCDs can resolve the detected X-ray into respective energy bins corresponding to respective energy ranges. The energy ranges for the respective bins are the same for all of the detector elements within the detector array. However, the optimal energy ranges for detector elements in one part of the X-ray beam will not necessarily be optimal for detector elements in another part of the X-ray beam because different parts of the X-ray beam can have different X-ray energy spectra. Thus, using the same ranges for the energy bins in all of the detector elements can degrade performance and image quality. Accordingly, better methods are desired to optimize the ranges (e.g., the energy thresholds and energy bin sizes) as a function of position within the X-ray beam.

BRIEF DESCRIPTION OF THE DRAWINGS

A more complete understanding of this disclosure is provided by reference to the following detailed description when considered in connection with the accompanying drawings, wherein.

DETAILED DESCRIPTION

Figure 1A:
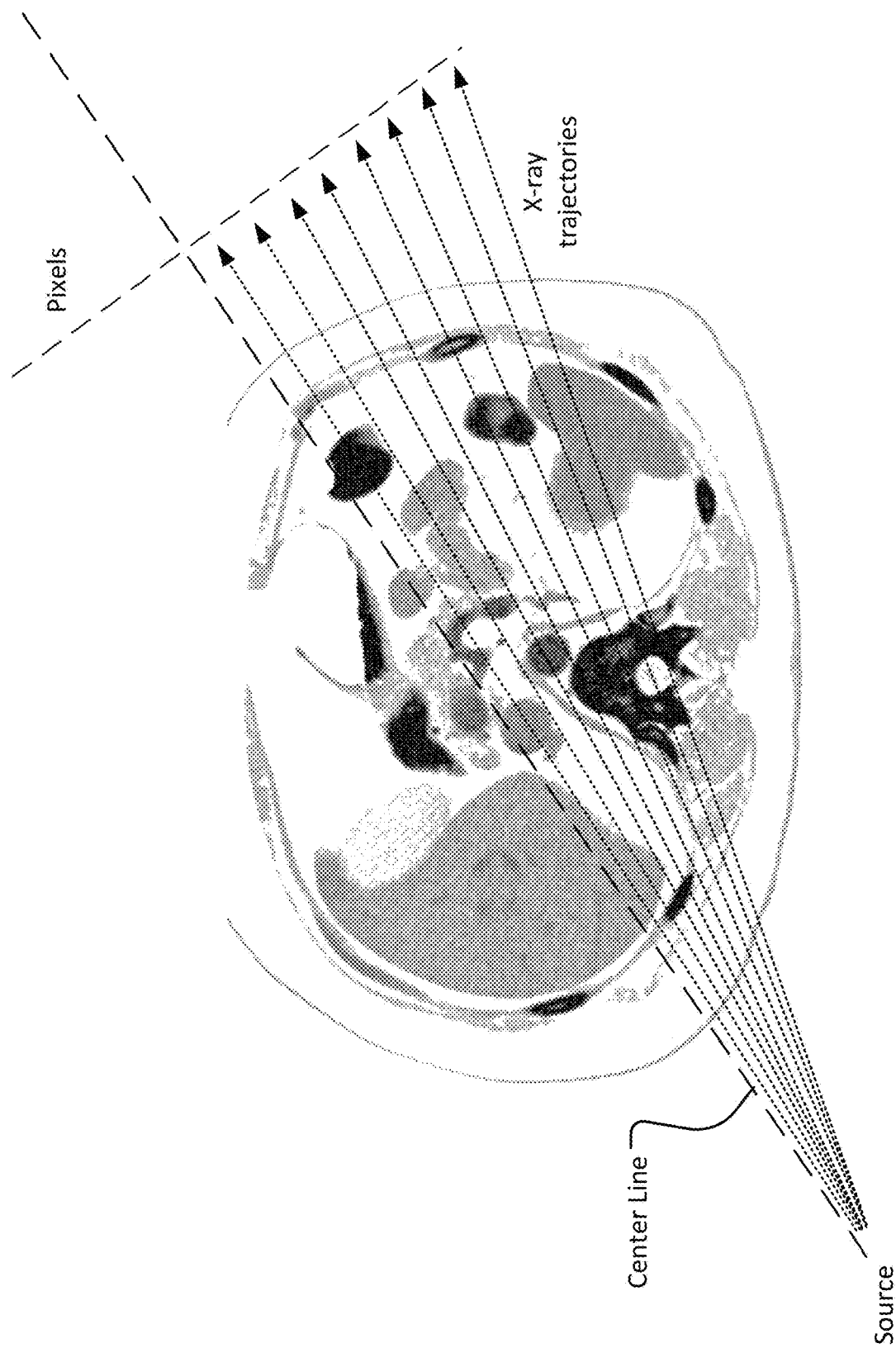
FIG. 1A shows a cross-section of an object (e.g. a patient, a torso, a phantom, etc.) and fanning X-ray trajectories originating from a source and passing through the object on their way to respective pixels or elements in a detector array.

The description set forth below in connection with the appended drawings is intended as a description of various aspects of the disclosed subject matter and is not necessarily intended to represent the only aspect(s). In certain instances, the description includes specific details for the purpose of providing an understanding of the disclosed subject matter. However, it will be apparent to those skilled in the art that aspects may be practiced without these specific details. In some instances, well-known structures and components may be shown in block diagram form in order to avoid obscuring the concepts of the disclosed subject matter.

Reference throughout the specification to "one aspect" or "an aspect" means that a particular feature, structure, characteristic, operation, or function described in connection with an aspect is included in at least one aspect of the disclosed subject matter. Thus, any appearance of the phrases "in one aspect" or "in an aspect" in the specification is not necessarily referring to the same aspect. Further, the particular features, structures, characteristics, operations, or functions may be combined in any suitable manner in one or more aspects. Further, it is intended that aspects of the disclosed subject matter can and do cover modifications and variations of the described aspects.

It must be noted that, as used in the specification and the appended claims, the singular forms "a,", and "the" include plural referents unless the context clearly dictates otherwise. That is, unless clearly specified otherwise, as used herein the words "a" and "an" and the like carry the meaning of "one or more." Additionally, it is to be understood that terms such as "top," "bottom," "front," "rear," "side," "interior," "exterior," and the like that may be used herein, merely describe points of reference and do not necessarily limit aspects of the disclosed subject matter to any particular orientation or configuration. Furthermore, terms such as "first," "second," "third," etc., merely identify one of a number of portions, components, points of reference, operations and/or functions as described herein, and likewise do not necessarily limit aspects of the disclosed subject matter to any particular configuration or orientation.

In photon counting CT, photon-counting detectors (PCDs) can detect the energy of each incident photon through direct conversion, for example via a CdTe or CZT energy resolving photon counting spectral detector. Compared to CT using an energy integrating detector (ETD), CT using a PCD provides additional energy-dependent information in the measurements, which enables material decomposition and spectral imaging.

The PCCT system's front-end electronics, such as an application specific integrated circuit (ASIC), convert the analog signal and compare it to pre-determined thresholds (voltages), which results in multiple energy bin count measurements. A photon-counting ASIC design may include, for example, 2-6 energy thresholds, with 2-6 energy bins. In some cases, a static value in the range of 25-50 key for the first threshold may be employed by some systems. However, there is a lack of methodology on how to determine the optimal energy thresholds since it may be dependent on system to system configuration settings. Notably, the lowest energy bin may include mixed data, including an attenuated primary X-ray beam and scattered X-rays. On one hand, the photoelectric interaction is the dominant attenuation mechanism at low energy range X-rays for the X-rays resulting in the low-energy X-rays exhibiting a higher sensitivity to material differences. On the other hand, the X-ray scattering X-rays process results in scattered X-rays having lower energy than the incident X-ray. Consequently, most of the scattered X-rays can be found in the low energy range, which contaminate the measurement and generate bias/artifacts in the CT image, unless X-ray scatter correction is performed. Selecting the optimal low-energy cut-off threshold is a tradeoff between excluding unwanted noise due to scattered X-rays by increasing the cut-off threshold and collecting as much signal as possible at the low X-ray energies by decreasing the cut-off threshold. Without determining the optimal energy thresholds and appropriate energy binning, valuable data may be excluded from the measurement. Thus, methods described herein optimize the PCCT system performance to enhance its clinical effectiveness by introducing dynamic, position-dependent energy thresholding and binning.

Referring now to the drawings, wherein like reference numerals designate identical or corresponding parts throughout the several views, FIG. 1A shows a cross-section of an object (e.g. a patient, a torso, a phantom, etc.) and diverging X-ray trajectories originating from a source and passing through the object on their way to respective pixels or elements in a detector array. Half of the X-ray trajectories are shown for simplicity, and the other half can be determined by reflecting the shown trajectories across the center line.

Some X-ray trajectories pass through only soft tissues, whereas the other X-ray trajectory passes through bone (e.g., a rib) in addition to passing through soft tissues. Moreover, for some source positions, such as directly overhead the patient, some of the X-ray trajectories may pass through only a patient's arms while others pass through the torso. As a corollary, for other source positions, such as to the left or right of the patient, some of the X-ray trajectories may first pass through a first arm, then the torso in a lateral orientation, followed by a second arm. Thus, the distance traveled by the X-ray and the material through which it travels is different for different positions of the source. Even for a perfectly round cylinder, some X-ray trajectories may pass through very little tissue, for example at the periphery, while other X-ray trajectories pass through the center of the object or patient. Some of these examples result in differences in attenuation between the central rays and the peripheral rays.

Figure 1B:
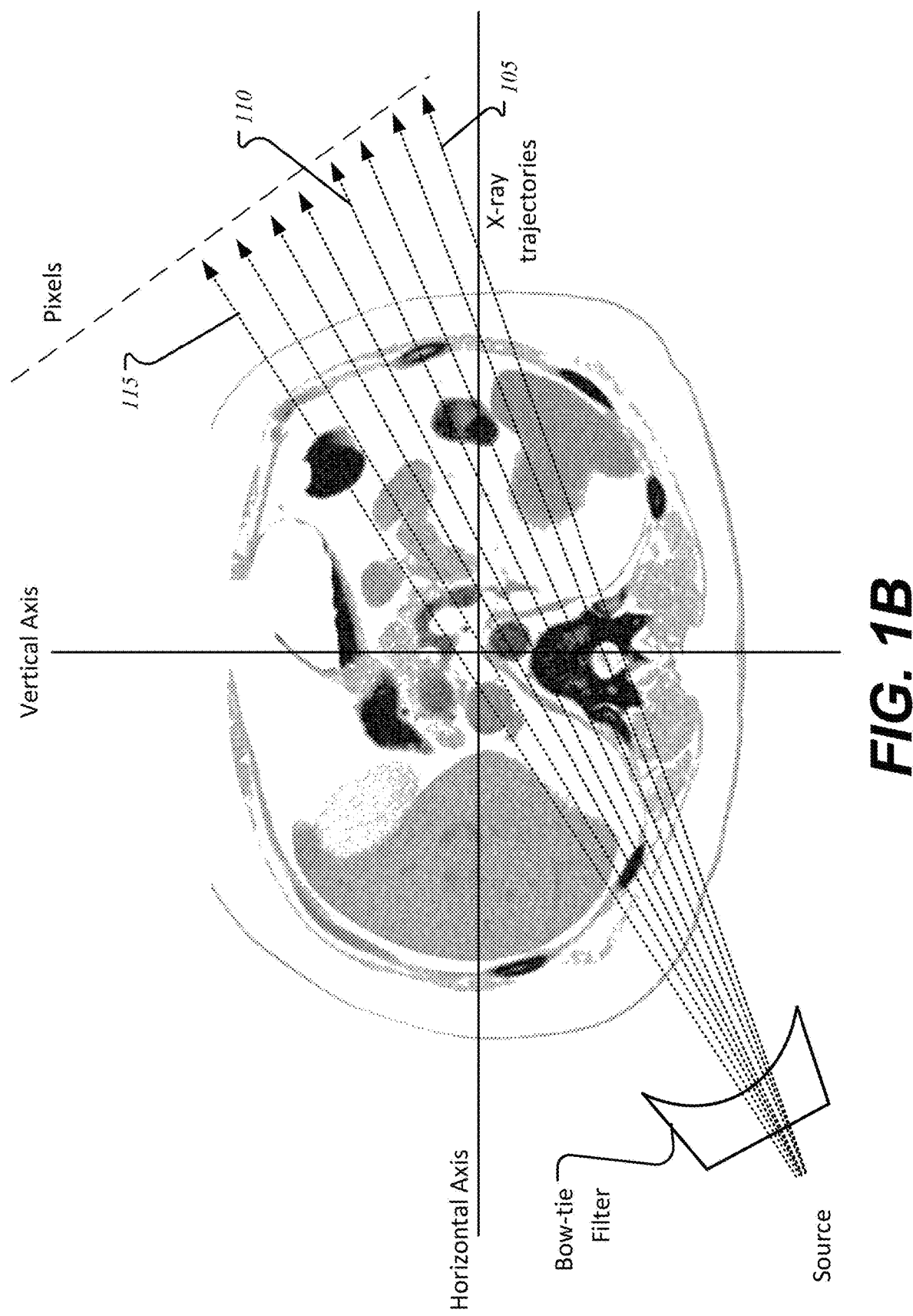
FIG. 1B shows a cross-section of a torso and fanning X-ray trajectories (herein referred to as "X-rays") with a bow-tie filter installed, according to an aspect of the present disclosure.

Further, to limit radiation dosage by shaping/narrowing the X-ray beam, a bow-tie filter may be added between the source and the patient. FIG. 1B shows a cross-section of a torso and fanning X-ray trajectories (herein referred to as "X-rays") with a bow-tie filter installed, according to an aspect of the present disclosure. In an aspect, the addition of a bow-tie filter may decrease the amount of X-rays directed towards the periphery of the patient, and may therefore reduce the radiation dose to the patient. For example, when taking a CT scan a head, a smaller fan angle might be desired in order to keep the X-ray dose as low as reasonably allowable. Similarly, for a cardiac CT scan, it might be desirable to decrease the radiation dose to the patient by decreasing dose to the parts of the body that are not clinically relevant, such as the arms. This may be accomplished via a shape of the bow-tie filter having edges that are thicker than a center of the bow-tie filter, wherein the bow-tie filter is installed such that X-rays directed towards the periphery of the fan angle pass through the thicker edges of the bow-tie filter and the central X-rays directed towards the center of the fan angle pass through the thinner center of the bow-tie filter. The bow-tie filter's pre-filtration of the beam introduces different spectrum along the fan angle. Hence without the scanning object or patient, detectors at the peripheral receive a spectrum that is shifted toward higher energies compared to detectors near the center.

Different beam shapes/widths can be advantageous for different clinical applications and patient size. Accordingly, the appropriate bow-tie filter can be selected from a discrete set of bow-tie filters based on the particular application and patient. In certain implementations, the energy spectra as a function of fan angle can be calibrated and stored for each appropriate bow-tie filter the discrete set bow-tie filters.

Figure 1C:
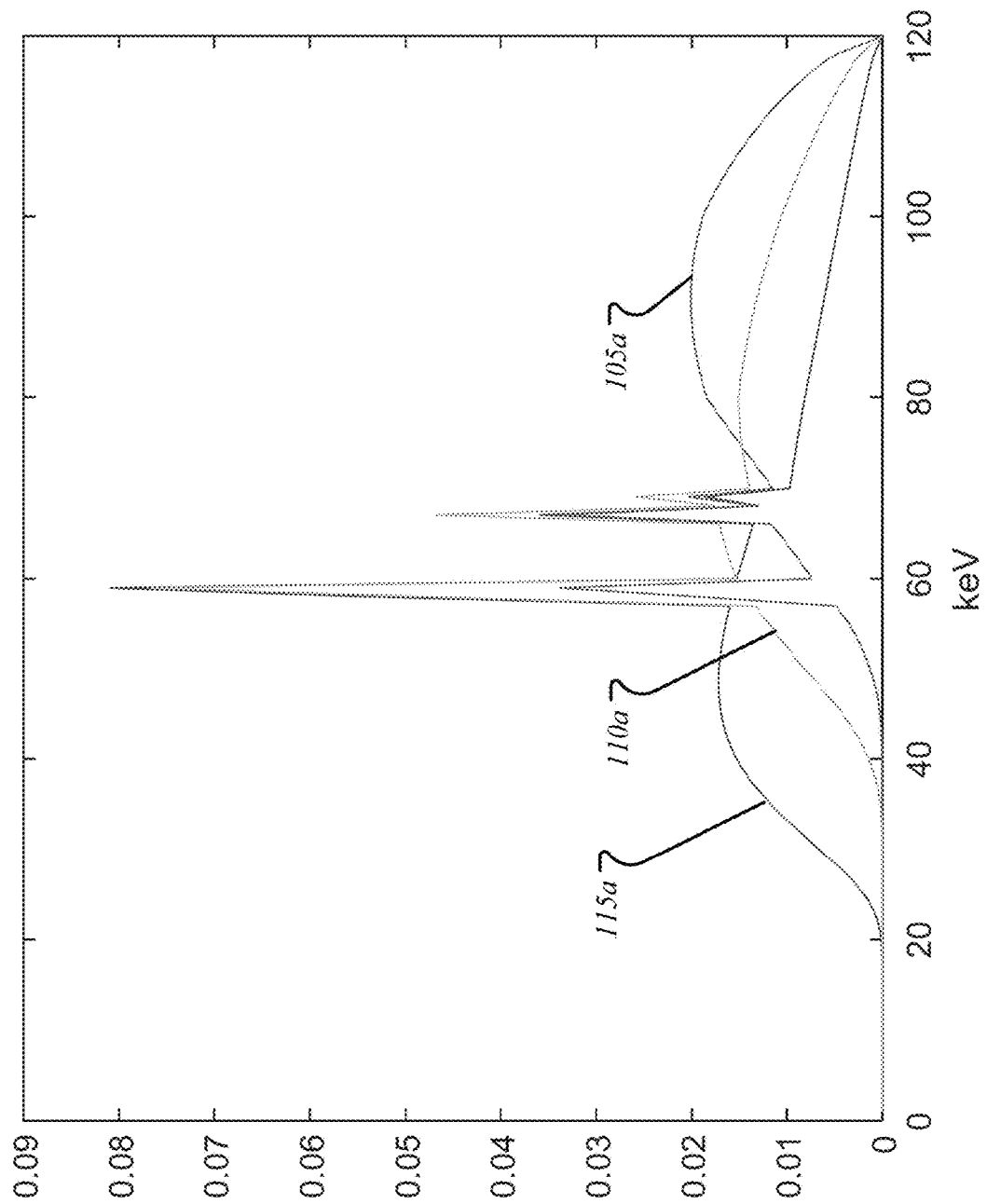
FIG. 1C shows example beam spectra after a bow-tie filter at different fan angles, according to an aspect of the present disclosure.

X-rays FIG. 1C shows a non-limiting example of beam spectra after the bow-tie filter at different fan angles. In FIG. 1C, an edge X-ray 105 produces the edge spectrum 105a, and a center X-ray 115 produces the center spectrum 115a. Further, an intermediate X-ray 110 produces the intermediate spectrum 110a. Due to the energy dependent attenuation of the bow-tie filter, the edge spectrum 105a is shifted towards higher energies more than the intermediate spectrum 110a, which is shifted more than the center spectrum 115a.

Figure 1D:
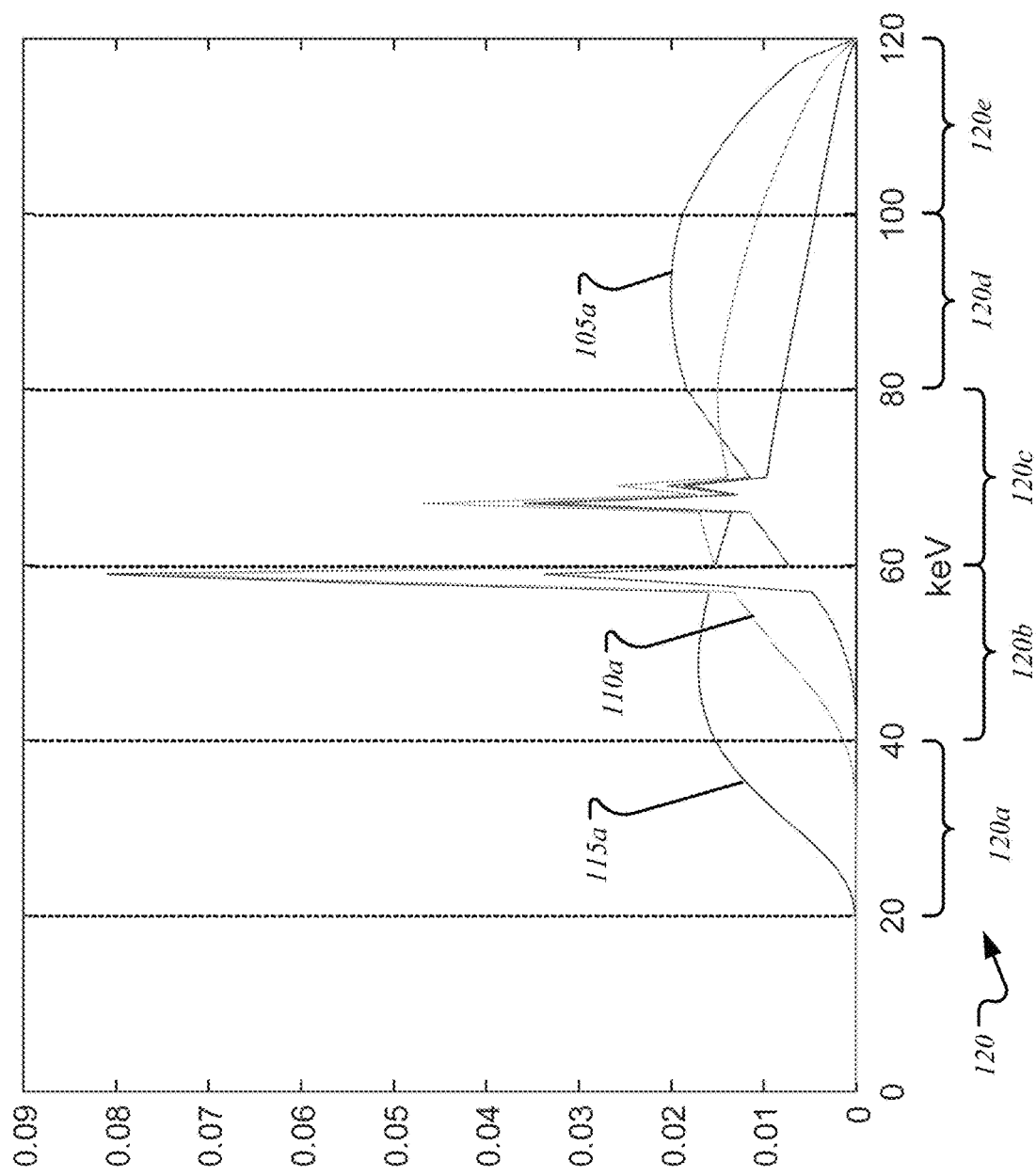
FIG. 1D shows example energy bins applied to example beam spectra after passing through a bow-tie filter at different fan angles, according to an aspect of the present disclosure.

FIG. 1D shows a non-limiting example of energy bins 120 applied to the example beam spectra after passing through the bow-tie filter at different fan angles. For example, thresholds defining the energy bins 120 may be set at predetermined energy levels. For example, thresholds may be set every 20 keV to yield a first energy bin 120a, a second energy bin 120b, a third energy bin 120c, a fourth energy bin 120d, and a fifth energy bin 120e. It may be appreciated by those in the art that various threshold levels and energy bin sizes may be employed. Notably, a pixel detecting the edge X-ray 105 may essentially receive no X-rays with energy lower than ~45 keV, while a pixel detecting the center X-ray 115 may receive X-rays with energy extending as low as ~20 keV. Therefore, the first energy bin 120a, as illustrated in FIG. 1D, may not provide substantial spectral information for the edge X-ray 105 since the edge spectrum 105a tails off at ~45 keV.

Accordingly, X-rays below 45 keV that are incident on the detector pixel corresponding to edge X-ray 105 are more likely to be from scatter than from the primary X-ray beam. Consequently, for this detector pixel, a low-energy cut-off threshold for the first energy bin 120a can be 50 keV, for example. In some implementations, this low-energy cut-off threshold can be moved down slightly (e.g., to 45 keV) to account for the finite energy resolution of the PCD (e.g., the energy resolution can be 5-10 keV). Additionally, in some implementations, the low-energy cut-off threshold might be moved up slightly to account for the additional attenuation resulting from propagating through the patient, especially when the patient is large and/or dense.

Regarding the detector pixels corresponding to the intermediate spectrum 110a low-energy cut-off threshold can be 40 keV, for example. Similar to the low-energy cut-off threshold for pixels corresponding to the edge spectrum 110a, the cut-off threshold of 40 keV can be adjusted up or down depending on the finite energy resolution of the PCD and the additional attenuation due to the patient.

Regarding the detector pixels corresponding to the center spectrum 115a, low-energy cut-off threshold can be 25 keV, for example. Similar to the low-energy cut-off threshold for pixels corresponding to the edge spectrum 105a, the cut-off threshold of 25 keV can be adjusted up or down depending on the finite energy resolution of the PCD and the additional attenuation due to the patient.

In view of the above, X-ray spectra and be simulated (or in some implementations measured/calibrated) for respective positions along the array of PCD pixels and these X-ray spectra can then be used to determine the low-energy cut-off threshold at the respective positions along the PCD array. That is, to optimize the threshold setting, configurable energy threshold settings may be applied to different pixels. Each individual pixel or group of pixels (e.g., a PCD module of 100 pixels) may include a configurable first energy threshold, additional configurable energy thresholds, and a method to automatically set the energy threshold values based on various inputs.

Figure 2:
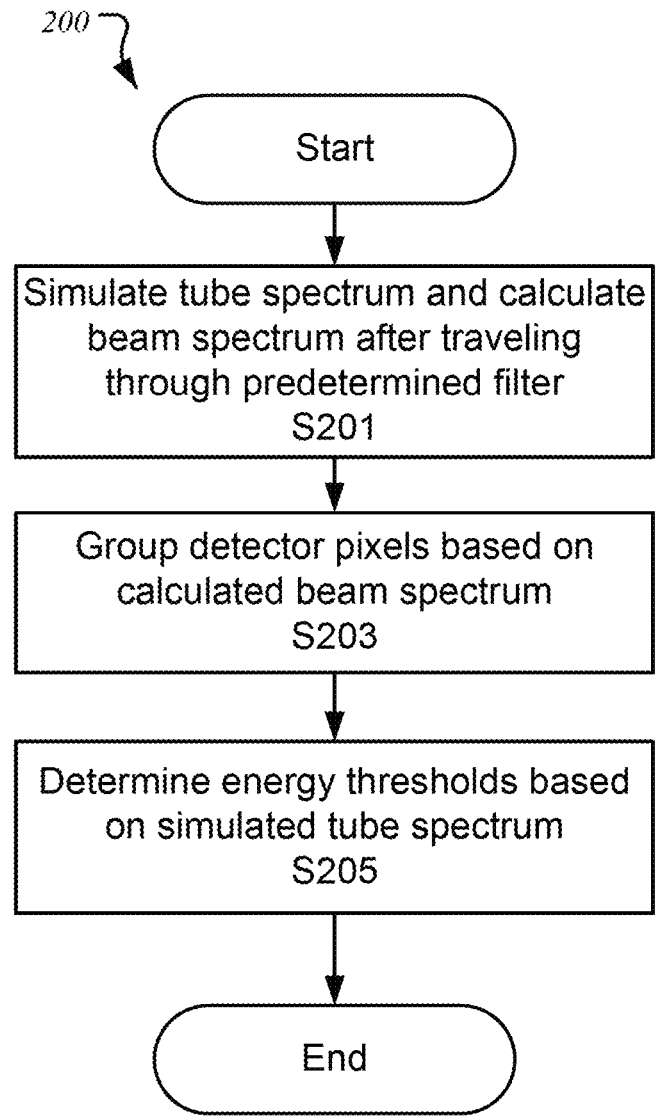
FIG. 2 shows a flow diagram of a method for configuring the energy thresholds via beam simulations and/or calibrations, according to an aspect of the present disclosure.

FIG. 2 is a flow diagram of a method 200 for configuring the energy thresholds via beam simulations and calibrations, according to an aspect of the present disclosure. In an aspect, the first energy thresholds across the pixels may be configured by using beam spectra that are estimated based on the energy-dependent attenuation arising from passing through the bow-tie filter. In step S201, the spectrum of the beam emitted from the source may be simulated and combined with the estimated attenuation of the beam spectrum passing through a predetermined filter. The estimated attenuation may be calculated based on the filter properties, such as geometry and material. For example, the predetermined filter may be a larger bow-tie filter for an adult patient, a smaller bow-tie filter for an adolescent patient, or another filter installed in the CT system for a particular clinical application.

In certain implementations, the spectrum of the beam emitted from the source may be based on calibration scans. Alternatively, the spectrum of the beam emitted from the source may be based on a simulation.

In step S203, the pixels in the detector array may optionally be grouped according to a desired coverage of the beam fan angles. For example, the detector array may include 896 rows/columns and a user nay desire to group 28 rows/columns together to yield 32 groups, covering the entire beam fan angle. Alternatively, the pixels can be grouped by modules. Further, each pixel can be its own group.

In step S205, the first energy threshold (i.e., the low-energy cut-off threshold) may be determined for each of the groups of pixels from step S203 based on the calculated beam spectrum. Thus, the first energy threshold can be unique for each group because the energy spectrum can be unique for each group.

In certain implementations, the center spectrum 115a may have a minimum energy. $E_{min}$, of 20 keV, and thus the first energy threshold for the pixel (or group of pixels) detecting the center X-ray 115 may be set at 20 keV. In another aspect, the PCDs may have an energy resolution, a, and the first energy threshold can be adjusted by an amount that is based on the energy resolution a. For example, the first energy threshold may be determined by subtracting the energy resolution from the minimum energy (e.g. $E_{min}$–a). That is, when the energy resolution is 5 keV and the minimum energy for the center spectrum 115a is 20 keV, the first energy threshold is set to 15 key.

Various methods can be used to determine the minimum energy $E_{min}$. In certain implementations, the minimum energy can be the energy for which the measured spectrum exceeds a predetermined threshold. For example, this predetermined threshold can be based on an absolute scale or relative values. The predetermined threshold can be relative to a peak of the energy spectrum or an integrated value of the energy spectrum, wherein the energy spectrum is expressed in count rate, irradiance, intensity, flux rate, etc. Alternatively, the minimum energy can be based on an integral of the energy spectrum. For example, the minimum energy can be selected to exclude a predetermined percentage (e.g., 2% or 5%) of the energy spectrum, which is measured, e.g., by either counts or energy. In certain implementations, the minimum energy is determined using both the energy spectrum and an estimate of the noise signal, such as a flux of scattered X-rays.

In another aspect, the other energy thresholds (e.g., the threshold between the first bin 120a and the second bin 120b or the threshold between the second bin 120b and the third bin 120c) may be determined/adjusted based on the position of the pixels.

Various rules can be used to determine the respective ranges of the energy bins. In the non-limiting example shown in FIG. 1D, the energy bins 120 each span the same energy range (i.e., 20 keV). Alternatively, the widths of energy bins can be selected to achieve noise balancing. Further, the widths of energy bins can be selected to equalize the number of counts or the signal to noise ratio among the energy bins. Additionally, the widths of energy bins can be selected according to some predefined formula based on the first energy threshold or based on a look-up-table. Moreover, other variations for selecting the widths of energy bins are within the spirit of the method.

For example, the first energy bin 120a of the center spectrum 105a may be 40 keV wide and span from 20 keV to 60 keV. The second energy bin 120b may be 20 key and span from 60 key to 80 keV. The third energy bin 120c may be 10 keV wide and span from 80 keV to 90 keV. The fourth energy bin 120d may be 10 key wide and span from 90 keV to 100 keV. The fifth energy bin 120e may be 20 keV wide and span from 100 keV to 120 keV, This would allow the first energy bin 120a to measure all the low energy X-rays, even those extending below 40 keV. Similarly, the adjusted third and fourth energy bins 120c, 120d would more precisely resolve the X-rays in the 80 to 100 keV range.

The various first energy thresholds and additional energy thresholds for all the groups of pixels may be calculated for each of the respective bow-tie filters (e.g. the larger bow-tie filter, the smaller bow-tie filter, etc.) and stored as a look-up-table. Thus, the look-up-table is saved as pre-set scan settings, and recalled based on which filter is used for a given scan. For example, the values may be stored as a pre-generated table in various formats, such as a look-up-table (LUT). Before the scan, based on the predetermined filter being used, the corresponding energy threshold setting may be applied to the pixels. Notably, this method may be performed during calibration stages for new filters before the patient is positioned on the gantry, saving the patient time during the scan.

Figure 3:
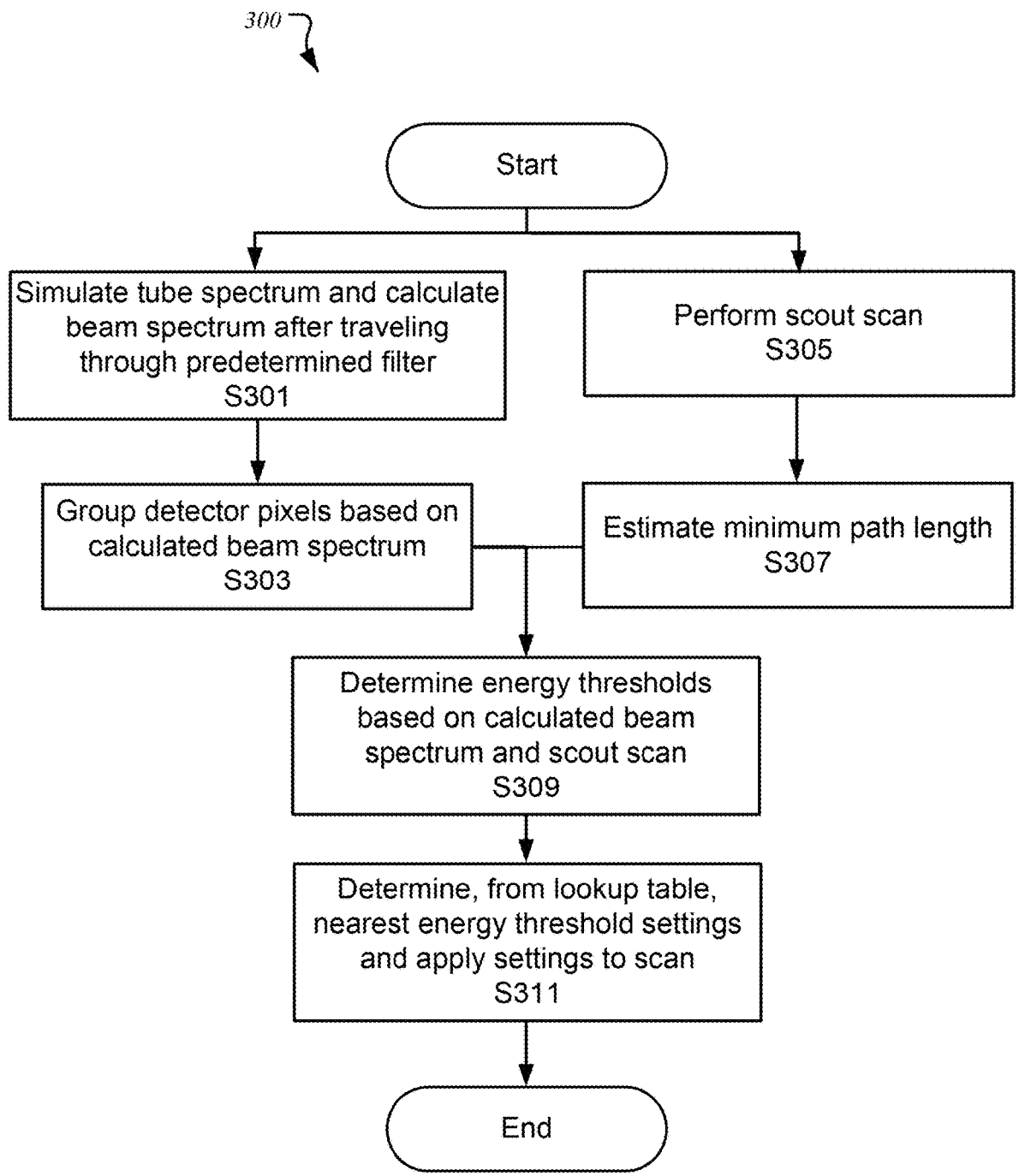
FIG. 3 shows a flow diagram for a method of configuring the energy thresholds via beam simulations and/or a preliminary scan, according to an aspect of the present disclosure.

FIG. 3 shows a non-limiting flow diagram for a method 300 of configuring the energy thresholds via beam simulations and a preliminary scan. In certain implementations, a scout scan may be performed to estimate a minimum path length between the source and the patient at various predetermined orientations around the patient. In this method, setting the first energy threshold for the pixels is based on more than just the design of the predetermined filter. The first energy threshold is further optimized by obtaining an estimate of the profile of the patient during the scout scan prior to the imaging scan. The first energy thresholds can then be adjusted based on the minimum path lengths determined for each view angle. That is, the energy spectrum can be simulated at respective view angles based on the combination of the attenuation arising from the minimum path lengths together with the calculated spectrum based on the beam filtration.

For example, the patient cross-section through the torso may be non-symmetric and have an ovular shape, wherein a horizontal axis diameter (relative to the ground) is longer than a vertical axis diameter. That is, the width of the torso from arm to arm may be wider than a thickness of the torso from spine to a front of the ribcage. Therefore, the minimum path length from the source to an exterior of the patient along the horizontal axis may be shorter than the minimum path length from the source to the exterior of the patient along the vertical axis.

In certain implementations, similar to method 200, in step S301 the tube spectrum may be simulated and the beam spectrum after traveling through the predetermined filter may be calculated based on the predetermined filter properties.

In step S303, the pixels in the detector array may optionally be grouped based on the calculated beam spectrum.

In step S305, the scout scan may irradiate the patient with a low dose at the predetermined orientations around the patient. To minimize radiation dose, the scout scan can include fewer view angles than an imaging scan. For example, the scout scan may irradiate the patient with the low dose along the vertical axis and separately with the low dose along the horizontal axis. It may be appreciated by those in the art that the scout scan may irradiate the patient with any number of low dose scans at various orientations in order to obtain an estimate of the patient's cross-sectional profile.

In step S307, the minimum path length is estimated based on the scout scan. In step S309, the minimum path length determined from the scout scan in combination with calculated beam spectrum after passing through the predetermined filter may be used to determine the first energy threshold. For example, the scout scan may determine the minimum path length along the horizontal axis is shorter and therefore the beam would be further attenuated by passing through more material (compared to, for example, a circular object). The calibration may, therefore, adjust the first energy threshold to higher energies across all groups of pixels based on the minimum path length determined via the scan taken at the horizontal axis.

In another aspect, the minimum path length determined from the scout scan in combination with calculated post-filter spectrum (i.e., the spectrum after passing through the predetermined filter) may be used to determine the first energy thresholds for various view angles (i.e., orientations of the X-ray source around the patient). That is, the first energy threshold may be determined at each view angle based on the minimum path length at that orientation. For example, the source oriented at the horizontal axis may determine via the scout scan that the minimum path length occurs at that orientation, and thus determines the first energy threshold for the center ray 115 for the source oriented at the horizontal axis is set at 20 keV. Subsequently, the source may rotate clock-wise by a predetermined, angle, for example 1 degree, and determine from the scout scan that, at a view angle of 1 degree above the horizontal axis, the minimum path length is slightly longer as compared to the scout scan at the horizontal axis. Based on said determination, the first energy threshold for the center ray 115 for the source oriented at the 1 degree-above horizontal axis orientation may be set to, for example, 21 keV, or preferably, greater than 20 keV.

In certain implementations, for view angles of the imaging scan that are different from view angles of the scout scan, the CT system can interpolate between (or extrapolate from) the nearest scout scan view angles to estimate the minimum path length. Further, interpolation/extrapolation can be used to determine energy spectra for view angles and positions along the fan angle (e.g., positions along the detector array) between which measured/simulated spectra are available.

In another aspect, the additional energy thresholds may also be further optimized by obtaining an estimate of the profile of the patient during the scout scan prior to the imaging scan and adjusting the additional energy thresholds based on the minimum path lengths at the respective view angles (in combination with the calculated spectrum based on the beam filtration). That is, based on the orientation of the source, the sizes of the energy bins 120 may be adjusted fore the groups of pixels at that particular orientation.

In another aspect, the first threshold and the additional energy thresholds for each of the groups of pixels may be adjusted according to the view angle (i.e., the orientation/position of the X-ray source). For example, during a scan where the source is oriented along the horizontal axis, the intermediate X-ray 110 may not pass through the patient. During a scan where the source is oriented along the vertical axis, the intermediate X-ray 110 may, due to the ovular shape of the patient's cross-section, pass through the patient, Thus, the orientation of the source around the patient affects the detected spectrum and potential additional attenuation of the beam as detected by the pixel detecting the intermediate X-ray 110 and its position along the fan angle.

A number of first energy threshold settings and additional energy threshold settings may be pre-defined, and calibrations may be generated for the pre-defined first energy threshold settings and additional energy threshold settings. The calibrations may be saved, for example, in the LUT.

In step S311 the CT system may determine a closest pre-defined first energy threshold setting from the LUT for each group of pixels in the detector array and apply the pre-defined first energy threshold settings to the imaging scan and subsequent data processing. Furthermore, the CT system may determine a closest pre-defined additional energy threshold setting from the LUT for each group of pixels in the detector array and apply the pre-defined additional energy threshold settings to the imaging scan and subsequent data processing.

In another aspect, the additional energy thresholds may also be further optimized by obtaining an estimate of the profile of the patient during the scout scan prior to the imaging scan and adjusting the additional energy thresholds based on the simulated spectra, which are calculated using the path lengths/attenuation at the respective view angles and fan angles in combination with the calculated, post bow-tie spectra as a function of fan angle.

In certain implementations, different groups of pixels can have different numbers of energy bins. For example, a center pixel group might have five energy bins, a peripheral pixel group might have three energy bins, and an intermediate pixel group might have four energy bins. That is, a number of the energy bins set for each group of pixels may be varied. If the first energy threshold for the pixel is set relatively high, keeping the size of the energy bins uniform and merely shifting them towards higher energies may result in the higher energy bins being compressed along the energy axis.

For example, the edge spectrum 105a may have the first energy threshold set at 40 keV, which may shift the fifth energy bin 120e to measure from 120 keV to 140 keV, where the spectrum does not include as much information. Thus, the fifth energy bin 120e may be eliminated altogether, resulting in four remaining energy bins 120. In another aspect, the energy bins 120 for edge detectors may be eliminated when the scan is set to scan a particular object in the patient where the edges of the patient contain less valuable information, for example a heart scan. Thus, one to two energy bins for the edge detectors may be eliminated. Often, when a pixel group has fewer energy bins than another pixel group, the pixel group with fewer energy bins will also have a higher value for the first energy threshold.

In summary, based on the complexity of the scan settings, an operator may wish to perform a faster scan and select predetermined first energy thresholds and additional energy thresholds based solely on the predetermined filter used. Similarly the operator may wish to perform a slower, more accurate scan and instruct the CT system to perform a course scout scan to determine the first energy threshold for all groups of pixels regardless of source orientation. The operator may wish to perform a fine scout scan for the slowest, most accurate scan, wherein the first energy threshold is adjusted on a view-by-view basis as the source rotates through all orientations arounds the patient.

The aforementioned aspects pertaining to reducing the number of energy bins provide a particular advantage for reducing the amount of the data being transmitted across a slip ring of the CT system. This reduction in the amount of date produced and transmitted is significant because the slip ring may have limited bandwidth.

Additionally, the aforementioned aspects hold benefit over CT systems with fixed first and fixed additional energy thresholds because the optimal first energy threshold and subsequent additional energy thresholds are determined for the groups of pixels based on the beam filtration and, in some aspects, the scout scan information. Therefore, each of the energy bins subsequently collects information from the imaging scan in the most effective and optimal manner.

Figure 4:
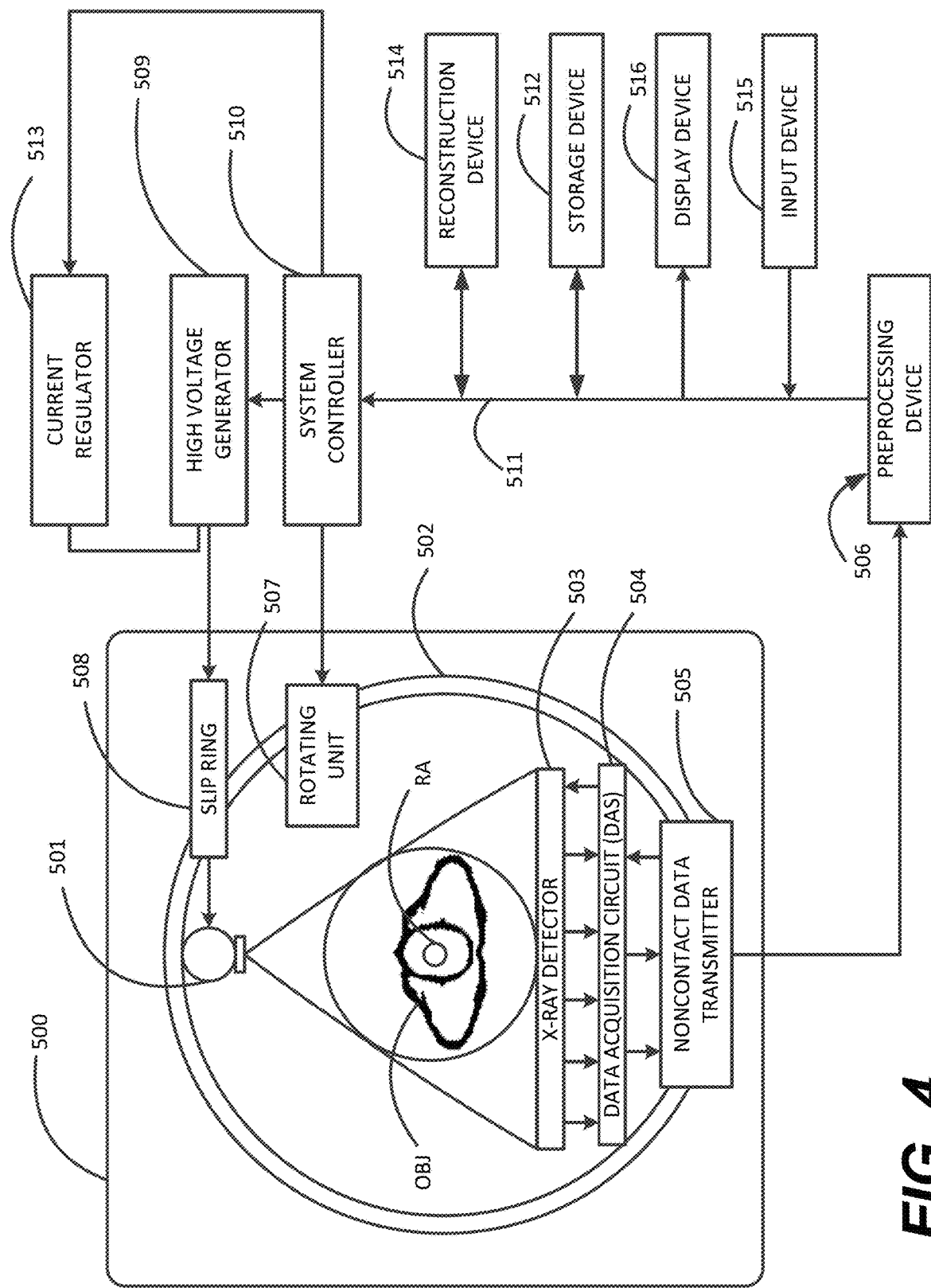
FIG. 4 shows a schematic of an implementation of a computed tomography scanner, according to an exemplary embodiment of the disclosure.

FIG. 4 shows a schematic of an implementation of a CT scanner according to an exemplary embodiment of the disclosure. Referring to FIG. 4, a radiography gantry 500 is illustrated from a side view and further includes an X-ray tube 501, an annular frame 502, and a multi-row or two-dimensional-array-type X-ray detector 503. The X-ray tube 501 and X-ray detector 503 are diametrically mounted across an object OBJ on the annular frame 502, which is rotatably supported around a rotation axis RA (or an axis of rotation). A rotating unit 507 rotates the annular frame 502 at a high speed, such as 0.4 sec/rotation, while the object OBJ is being moved along the axis RA into or out of the illustrated page.

X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present disclosure can be applied to either type. The rotate/rotate type will be used as an example for purposes of clarity.

The multi-slice X-ray CT apparatus further includes a high voltage generator 509 that generates a tube voltage applied to the X-ray tube 501 through a slip ring 508 so that the X-ray tube 501 generates X-rays. The X-rays are emitted towards the object OBJ, whose cross sectional area is represented by a circle. For example, the X-ray tube 501 having an average X-ray energy during a first scan that is less than an average X-ray energy during a second scan. Thus, two or more scans can be obtained corresponding to different X-ray energies. The X-ray detector 503 is located at an opposite side from the X-ray tube 501 across the object OBJ for detecting the emitted X-rays that have transmitted through the object OBJ. The X-ray detector 503 further includes individual detector elements or units.

The CT apparatus further includes other devices for processing the detected signals from X-ray detector 503. A data acquisition circuit or a Data Acquisition System (DAS) 504 converts a signal output from the X-ray detector 503 for each channel into a voltage signal, amplifies the signal, and further converts the signal into a digital signal. The X-ray detector 503 and the DAS 504 are configured to handle a predetermined total number of projections per rotation (TPPR). The DAS 504 can include a comparator with configurable energy thresholds to discriminate the detected counts into energy bins. These energy levels can be set by the various steps in methods 110, 150, 200, and 300 described herein.

The above-described data is sent to a preprocessing device 506, which is housed in a console outside the radiography gantry 500 through a non-contact data transmitter 505. The preprocessing device 506 performs certain corrections, such as sensitivity correction on the raw data, A memory 512 stores the resultant data, which is also called projection data, at a stage immediately before reconstruction processing. The memory 512 is connected to a system controller 510 through a data/control bus 511, together with, a reconstruction device 514, input device 515, and display 516. The system controller 510 controls a current regulator 513 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 501 and the X-ray detector 503 are diametrically mounted on the annular frame 502 and are rotated around the object OBJ as the annular frame 502 is rotated about the rotation axis RA. In the fourth-generation geometry system, the detectors are fixedly placed around the patient and an X-ray tube rotates around the patient. In an alternative embodiment, the radiography gantry 500 has multiple detectors arranged on the annular frame 502, which is supported by a C-arm and a stand.

The memory 512 can store the measurement value representative of the irradiance of the X-rays at the X-ray detector unit 503. Further, the memory 512 can store a dedicated program for executing, for example, various steps of the methods 110, 150, 200, and 300 for training a neural network and reducing imaging artifacts.

The reconstruction device 514 can execute various steps of the methods 110, 150, 200, and 300. Further, reconstruction device 514 can execute pre-reconstruction processing image processing such as volume rendering processing and image difference processing as needed.

The pre-reconstruction processing can include various of the steps of methods 110, 150, 200, and 300. Additionally, the pre-reconstruction processing of the projection data performed by the preprocessing device 506 can include correcting for detector calibrations, detector nonlinearities, and polar effects, for example.

Post-reconstruction processing performed by the reconstruction device 514 can include filtering and smoothing the image, volume rendering processing, and image difference processing as needed. The image reconstruction process can implement various CT image reconstruction methods. The reconstruction device 514 can use the memory to store, e.g., projection data, reconstructed images, calibration data and parameters, and computer programs.

The reconstruction device 514 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 512 can be non-volatile, such as ROM, EPROM, EEPROM or FLASH memory. The memory 512 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction device 514 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA. UNIX, Solaris. LINUX, Apple, MAC-OS and other operating systems known to those skilled in the art. Further CPU can be implemented as multiple processors cooperatively working in parallel to perform the instructions.

In one implementation, the reconstructed images can be displayed on a display 516. The display 516 can be an LCD display, CRT display, plasma display, OLED, LED or any other display known in the art.

The memory 512 can be a hard disk drive, CD-ROM drive, DVD drive, FLASH drive, RAM, ROM or any other electronic storage known in the art.

The PCDs can use a direct X-ray radiation detectors based on semiconductors, such as cadmium telluride (CdTe), cadmium zinc telluride (CZT), silicon (Si), mercuric iodide ($HgI_2$), and gallium arsenide (GaAs). Semiconductor based direct X-ray detectors generally have much faster time response than indirect detectors, such as scintillator detectors. The fast time response of direct detectors enables them to resolve individual X-ray detection events. However, at the high X-ray fluxes typical in clinical X-ray applications some pile-up of detection events will occur. The energy of a detected X-ray is proportional to the signal generated by the direct detector, and the detection events can be organized into energy bins yielding spectrally resolved X-ray data for spectral CT.

While certain implementations have been described, these implementations have been presented by way of example only, and are not intended to limit the teachings of this disclosure. Indeed, the novel methods, apparatuses and systems described herein can be embodied in a variety of other forms; furthermore, various omissions, substitutions and changes in the form of the methods, apparatuses and systems described herein can be made without departing from the spirit of this disclosure.

The invention claimed is:

1. An imaging apparatus, comprising:
   circuitry configured to
   estimate, for two or more detector elements in an array of photon-counting detector elements, respective energy spectra of an X-ray beam incident on the corresponding detector elements, the energy spectra being estimated by modeling an X-ray attenuation as a function of X-ray energy;
   set, for each detector element of the two or more detector elements, a first energy threshold of a first energy range that is detected by the each detector element, the first energy threshold of the each detector element being based on the estimated energy spectra of the each detector element, including
   set a number of energy bins of a first detector element of the two or more detector elements to be less than a number of energy bins of a second detector element of the two or more detector elements, the number of energy bins of a first detector element being two or greater, wherein a first energy threshold of the first detector element is greater than a first energy threshold of the second detector element; and
   signal that a detected X-ray by one of the two or more detector elements falls within a first energy bin when a measured energy of the detected X-ray is less than a second energy threshold and greater than the first energy threshold of the one of the two or more detector elements.

2. The imaging apparatus according to claim 1, wherein the circuitry is further configured to estimate the respective energy spectra by modeling X-ray attenuation wherein an X-ray beam is transmitted through a filter.

3. The imaging apparatus according to claim 2, wherein the circuitry is further configured to estimate the respective energy spectra by modeling X-ray attenuation wherein the X-ray beam is transmitted through the filter and an object.

4. The imaging apparatus according to claim 3, wherein the circuitry is further configured to estimate the respective energy spectra by the modeling the energy spectra based on simulations of the X-ray beam transmitted through the filter and the object.

5. The imaging apparatus according to claim 3, wherein the circuitry is further configured to estimate the respective energy spectra by the modeling the energy spectra based on calibrations of the X-ray beam transmitted through the filter and based on simulations of the X-ray beam transmitted through the object.

6. The imaging apparatus according to claim 3, wherein the circuitry is further configured to estimate the respective energy spectra of the X-ray beam by determining, at one view angle, an attenuation projection length of the X-ray beam transmitted through the object and use the attenuation projection length to simulate the X-ray beam transmitted through the object at a plurality of view angles.

7. The imaging apparatus according to claim 6, wherein the attenuation projection length at the one view angle is a minimum or a maximum attenuation projection length of the plurality of view angles.

8. The imaging apparatus according to claim 3, wherein the circuitry is further configured to estimate the respective energy spectra of the X-ray beam by determining, at each view angle, an attenuation projection length of the X-ray beam transmitted through the object and use the attenuation projection length at the respective view angles to simulate the X-ray beam transmitted through the object at the corresponding view angles.

9. The imaging apparatus according to claim 1, wherein the circuitry is further configured to set, for each detector element of the two or more detector elements, a plurality of additional energy thresholds delineating boundaries of respective energy bins, the additional energy thresholds including a second energy threshold between the first energy bin and a second energy bin.

10. The imaging apparatus according to claim 9, wherein spectral widths of the energy bins are non-uniform.

11. The imaging apparatus according to claim 1, wherein the circuitry is further configured to group the detector elements into a plurality of groups, each group of the plurality of groups having a respective energy spectrum of the X-ray beam, and each group of the plurality of groups setting the first energy threshold based on the corresponding energy spectrum.

12. The imaging apparatus according to claim 1, further comprising
the detector elements of an X-ray source, each detector element including a comparator that compares a signal generated upon detection of an X-ray with a plurality of signal thresholds corresponding to respective energy thresholds, which include the first energy threshold, and the each detector element indicating that a detected X-ray has an energy in the first energy bin when the signal generated upon detection of an X-ray is greater than a first signal threshold and less than a second signal threshold of the plurality of signal thresholds.

13. A method, comprising:
estimating, for two or more detector elements in an array of photon-counting detector elements, respective energy spectra of an X-ray beam incident on the corresponding detector elements, the energy spectra being estimated by modeling an X-ray attenuation as a function of X-ray energy;
setting, for each detector element of the two or more detector elements, a first energy threshold of a first energy range that is detected by the each detector element, the first energy threshold of the each detector element being based on the estimated energy spectra of the each detector element, including
setting a number of energy bins of a first detector element of the two or more detector elements to be less than a number of energy bins of a second detector element of the two or more detector elements, the number of energy bins of a first detector element being two or greater, wherein a first energy threshold of the first detector element is greater than a first energy threshold of the second detector element; and
signaling that a detected X-ray by one of the two or more detector elements falls within a first energy bin when a measured energy of the detected X-ray is less than a second energy threshold and greater than the first energy threshold of the one of the two or more detector elements.

14. The method according to claim 13, wherein estimating the respective energy spectra is performed by modeling X-ray attenuation of an X-ray beam that is transmitted through a filter and an object.

15. The method according to claim 14, wherein estimating the respective energy spectra is performed by modeling the X-ray attenuation through the object based on simulations of the X-ray beam transmitted through the filter and the object.

16. The method according to claim 14, wherein estimating the respective energy spectra is performed by modeling the X-ray attenuation through the object using a scout scan in which scout projection data is acquired using a lower radiation dose than in used for a latter imaging scan.

17. The method according to claim 13, further comprising setting, for each detector element of the two or more detector elements, a plurality of additional energy thresholds delineating boundaries of respective energy bins, the additional energy thresholds including a second energy threshold between the first energy bin and a second energy bin.

18. A non-transitory computer-readable medium storing executable instructions, wherein the instructions, when executed by processing circuitry, cause the processing circuitry to perform the method according to claim 13.

* * * * *